United States Patent [19]

Sifniades et al.

[11] 4,259,239

[45] Mar. 31, 1981

[54] RESOLUTION OF ENANTIOMERIC COMPLEXES OF NICKELOUS CHLORIDE AND ALPHA-AMINOCAPROLACTAM

[75] Inventors: Stylianos Sifniades, Madison; Meir Lahav, Berkeley Heights; William J. Boyle, Jr., Warren, all of N.J.

[73] Assignee: Allied Chemical Corporation, Morris Township, Morris County, N.J.

[21] Appl. No.: 142,530

[22] Filed: Apr. 21, 1980

[51] Int. Cl.$^3$ .................. C07D 223/10; C07D 223/12
[52] U.S. Cl. ............................................. 260/239.3 R
[58] Field of Search ................................. 260/239.3 R

[56] References Cited

U.S. PATENT DOCUMENTS

| | | | |
|---|---|---|---|
| 3,941,776 | 3/1976 | Sifniades et al. | 260/239.3 R |
| 3,988,320 | 10/1976 | Sifniades et al. | 260/239.3 R |
| 4,062,839 | 12/1977 | Sifniades et al. | 260/239.3 R |

*Primary Examiner*—Henry R. Jiles
*Assistant Examiner*—Robert T. Bond

*Attorney, Agent, or Firm*—Robert A. Harman

[57] ABSTRACT

A racemic mixture of D- and L- forms of alpha-aminocaprolactam ("ACL") dissolved in e.g. ethanol is resolved, and preferably the undesired form remaining is solution is simultaneously racemized, by forming a supersaturated solution of the D,L-(ACL)$_3$NiCl$_2$.EtOH complex; providing an optically active form of lysine (e.g. L-lysine) as crystallization inhibitor of the undesired enantiomer of said complex (e.g. the D-form), and crystallizing a portion of the desired form of the complex from the solution. The undesired form remaining in solution can be simultaneously racemized by providing a strong base and an excess of ACL over the stoichiometric proportion required to form the complex. The recovered crystals of the desired form of the complex can be processed to afford the desired form of ACL, and to recover the nickel reagent. The ACL can be converted to the desired form of lysine, a nutritionally valuable amino acid.

4 Claims, No Drawings

4,259,239

RESOLUTION OF ENANTIOMERIC COMPLEXES OF NICKELOUS CHLORIDE AND ALPHA-AMINOCAPROLACTAM

BACKGROUND OF THE INVENTION

It is known that alpha-aminocaprolactam ("ACL") exists in the form of enantiomeric optical isomers, the D-form and the L-form. It is further known that the racemic mixture of these forms can be resolved, i.e. separated, by producing the D, L- (i.e. racemic) mixture of the aminocaprolactam complex with nickelous chloride in situ in solution, at concentration resulting in supersaturation; then preferentially crystallizing the desired form, e.g. the L-form, from such solution by use of seed crystals of the desired form. It is also known that when the complex with nickelous chloride is used for such resolution, conditions can be adopted under which the racemization of the undesired form of the complex into the desired form proceeds simultaneously with the resolution process. The resulting desired enantiomer of the complex can then be decomposed to afford the desired alpha-aminocaprolactam enantiomer; and this enantiomer can be converted to the corresponding enantiomer of lysine e.g. to L-lysine, a valuable nutritional product. See U.S. Pat. No. 3,988,320 of Oct. 26, 1976 to Sifniades, Boyle, and Van Peppen.

The process of resolution of the enantiomer mixture and simultaneous racemization of the undesired enantiomer to replenish the mixture, described in the above patent, is a useful advance in the art. However, it would be desirable to obtain the results of that patent without necessity of using seed crystals of the desired enantiomeric form of the complex at the startup, when the mixture of D- and L-enantiomers is the racemic mixture.

The present invention enables resolution of racemic mixtures of the nickelous chloride complexes with alpha-aminocaprolactam without use of seed crystals of the desired enantiomer of the ACL/NiCl$_2$ complex.

SUMMARY OF THE INVENTION

This invention consists essentially in a process for resolution of a mixture of D- and L-forms of tris(alpha-aminocaprolactam) NiCl$_2$. ROH—wherein R is methyl, ethyl, or isopropyl—to increase the ratio of one form of the aminocaprolactam/nickel chloride complex in the crystalline product obtained, as compared to the ratio in the starting material. Preferably the undesired form of the complex is simultaneously racemized, under conditions such as described in U.S. Pat. Nos. 3,941,776 of Mar. 2, 1976 and 3,988,320 of Oct. 26, 1976 both to Sifniades, Boyle, and Van Peppen. Such conditions provide for presence of a strong base, and utilize an excess of aminocaprolactam over that stoichiometrically required for formation of the complex (ACL)$_3$NiCl$_2$.

The present process comprises forming a supersaturated solution of said complex; including one optically active form of lysine in said solution, namely L-lysine as crystallization inhibitor of the D-form of said complex when the L-form is desired and D-lysine when the D-form of the complex is desired; and crystallizing a portion of the complex from said supersaturated solution. More specifically since L-lysine is the commonly desired enantiomer of lysine, L-lysine is included in the saturated solution of the alpha-aminocaprolactam/nickelous chloride complex enantiomers in the range between 1 mol percent and 20 mol percent based on the content of the complex in the solution. We have found that such addition of L-lysine has an inhibitory effect on the crystallization, from the supersaturated solution, of the D-form of the complex in solution; so that the crystals precipitated are therefore enriched in the L-form of the complex.

DETAILED DESCRIPTION

This invention can be used to produce a crystalline product enriched in the desired enantiomer of the alpha-aminocaprolactam nickel chloride complex without use of seed crystals of the desired enantiomer, although desirably seed crystals of the racemic form of the complex are used. The invention is especially useful to allow starting up a process of resolving a racemic mixture of the D- and L-forms of said complex by preferentially repressing crystallization of the undesired enantiomer, e.g. the D-form of the complex. Once the process is started, the precipitated crystals rich in the L-form of the complex can function as seed crystals in carrying out procedures, described in the above cited U.S. Pat. No. 3,988,320, whereby to obtain simultaneous resolution and racemization of the dissolved ACL/NiCl$_2$ enantiomeric complexes.

The examples which follow are illustrative of the present invention but are not to be interpreted in a limiting sense.

EXAMPLE 1

An ethanol solution was made up to contain 25 g (ACL)$_3$NiCl$_2$. EtOH per 100 ml of total volume using 4.5 moles of ACL per mole of NiCl$_2$ plus 0.033 mole of lithium ethoxide base per mole of ACL and 0.047 mole of L-lysine per mole of ACL all dissolved in ethanol. A 2 mL aliquot of the solution was placed in a sealed vial and heated in an 80° C. oil bath for 72 h. No crystallization was evident during that period. Then 2 mg of D,L-(ACL)$_3$NiCl$_2$. EtOH (i.e. racemic) seed crystals were added and heating was resumed. After 48 h from the addition of the seed crystals, 57 mg of crystalline L-(ACL)$_3$NiCl$_2$. EtOH had formed, and was recovered by filtration. The optical rotation [$\alpha$] of these product crystals was $[\alpha]_D^{20} = -12.7°$ (c 4, 1N HCl), corresponding to 54% excess of L-ACL complex over D-ACL complex in the product crystals.

EXAMPLES 2–7

In a similar manner experiments were performed, also at 80° C. and 2 mL volume, with other concentrations and mole ratios. The conditions and results of all these experiments are summarized in Table 1 below. In all cases when L-lysine was added, the product crystals contained an excess of L-ACL complex over D-ACL complex. In comparison examples 4 and 6, in which no L-Lysine was added, the product crystals were the racemic compound.

TABLE 1

| | L-Lysine Assisted Resolution of (ACl)$_3$NiCl$_2$ . EtOH Complex | | | |
|---|---|---|---|---|
| (A) Example No. | Conc. of Complex g/100 mL | Mole Ratio ACL/Ni | Mole Ratio Lysine/ACL | Mole Ratio Li/ACL |
| 1 | 25 | 4.5 | 0.047 | 0.033 |
| 2 | 20 | 3.5 | 0.088 | 0.29 |
| 3 | 20 | 3.5 | 0.088 | 0 |
| 4 | 20 | 3.5 | 0 | 0.029 |
| 5 | 25 | 3.5 | 0.020 | 0.028 |

TABLE 1-continued

L-Lysine Assisted Resolution of $(ACl)_3NiCl_2 \cdot EtOH$ Complex

| | | | | |
|---|---|---|---|---|
| 6 | 25 | 3.5 | 0 | 0.028 |
| 7 | 25 | 3.5 | 0.051 | 0.028 |

(B)

| Example No. | Time h | Racemic Comp'd Seed mg | Precipitated Product Total mg | Excess L-,%* |
|---|---|---|---|---|
| 1 | 48 | 2 | 57 | 54 |
| 2 | 24 | 2 | 9 | 67 |
| 3 | 24 | 0 | 75 | 10 |
| 4 | 24 | 0 | 155 | 0 |
| 5 | 18 | 0 | 273 | 11 |
| 6 | 18 | 0 | 223 | 0 |
| 7 | 18 | 0 | 468 | 16 |

Volume in Example 7 was 5 mL initially and was concentrated to 3.5 mL after 24 h.
*Percent of L-complex minus percent of D-complex in product crystals.

Further experiments similarly conducted are summarized in Tables 2 and 3 below. In all these runs, lithium ethoxide was added in molar excess over the lysine taken, thus providing free strong base in the reaction mixture. (The carboxyl group of the lysine reduces the amount of base present by reaction to form the equivalent amount of salt). Moreover, the ACL taken was in excess of the 3 moles per mole of $NiCl_2$, stoichiometrically required for formation of the complex, $(ACL)_3NiCl_2 \cdot EtOH$. Under these conditions, simultaneous racemization of complex occurred in solution along with the resolution process, so that the ACL remaining in the solution after removal of the crystallized product was essentially racemic.

TABLE 2

L-Lysine Assisted Resolution of $(ACL)_3NiCl_2 \cdot EtOH$

| Example No. | Seeds mg | Enantiomer | Total Product mg$^{(a)}$ | $[\ ]_D$ | % Excess$^{(b)}$ Enantiomer |
|---|---|---|---|---|---|
| 8 | 5.0 | D,L- | 32.9 | −14.0 | 60% L- |
| 9 | 4.9 | L- | 36.7 | −22.3 | 96% L- |
| 10 | 5.1 | D- | 20.8 | +22.6 | 97% D- |

Conditions: 80° C., 2 mL volume, 23 h. Concentration of complex, 25 g/100 mL; mole ratios ACL/Ni = 3.5; L-Lysine/ACL = 0.10; LiOEt/ACL = 0.13.

$^{(a)}$Combined seeds and precipitated crystals
$^{(b)}$Percent of stated $(ACL)_3NiCl_2 \cdot EtOH$ enantiomer minus percent of the other enantiomer in the product crystals

TABLE 3

D-Lysine Assisted Resolution of D,L-$(ACL)_3NiCl_2 \cdot EtOH$

| Example No. | Mole Ratios D-Lys/ACL | LiOEt/ACL | Seeds mg D,L- | Total Product mg$^{(a)}$ | % Excess D-$^{(b)}$ |
|---|---|---|---|---|---|
| 11 | 0.10 | 0.13 | 5.0 | 19.9 | 52 |
| 12 | 0.052 | 0.0795 | 5.1 | 79.7 | 44 |
| 13 | 0.021 | 0.049 | 5.2 | 254 | 27 |
| 14 | 0.021 | 0.049 | 0 | 203 | 23 |

Conditions: 80° C., 2 mL volume, 19 h. Concentration of complex, 25 g/100 mL; ACL/Ni = 3.5 mole ratio $^{(a)}$Seeds plus precipitate
$^{(b)}$Percent of D-$(ACL)_3NiCl_2 \cdot EtOH$ minus percent of L- in product crystals Experiments similarly conducted to show the effect of L-lysine and of D-lysine on the rate of resolution of the complex are summarized in Tables 4–6 below. In all these experiments the seed crystals were L-$(ACL)_3NiCl_2 \cdot EtOH$ taken from a single preparation, and the experimental conditions were essentially identical.

TABLE 4

Kinetics of Resolution of $(ACL)_3NiCl_2 \cdot EtOH$ in the Presence of L-Lysine

| Example No. | Time Min. | Seeds (L-) mg$^{(b)}$ | Total Product mg$^{(a)}$ | % Excess L-$^{(c)}$ | mg L-$^{(d)}$ | L-Growth Factor$^e$ |
|---|---|---|---|---|---|---|
| 15 | 10 | 19.8 | 47.8 | 98 | 47.3 | 2.38 |
| 16 | 20 | 19.8 | 72.3 | 91 | 69.0 | 3.47 |
| 17 | 30 | 19.9 | 79.3 | 91 | 75.7 | 3.79 |
| 18 | 40 | 19.7 | 71.3 | 77 | 80.8 | 4.10 |

Conditions: 80° C., 2 mL volume. Concentration of complex, 25 g/100 mL. Mole ratios ACL/Ni = 3.05; L-Lysine/ACL = 0.02; LiOEt/ACL = 0.02.

$^{(a)}$Seeds plus precipitate
$^{(b)}$mg of L-$(ACL)_3NiCl_2 \cdot EtOH$ used as seed crystals in the experiment
$^{(c)}$Percent of L-$(ACL)_3NiCl_2 \cdot EtOH$ minus percent of D- in product crystals
$^{(d)}$mg of L-$(ACL)_3NiCl_2 \cdot EtOH$ in product crystals
$^{(e)}$mg of L- in product crystals/mg seed crystals

TABLE 5

Kinetics of Resolution of $(ACL)_3NiCl_2 \cdot EtOH$ in the Presence of D-Lysine

| Example No. | Time Min. | Seeds (L-) mg$^{(b)}$ | Total Product mg$^{(a)}$ | % Excess L-$^{(c)}$ | mg L-$^{(d)}$ | L-Growth Factor$^{(e)}$ |
|---|---|---|---|---|---|---|
| 19 | 10 | 19.9 | 42.9 | 95 | 41.8 | 2.09 |
| 20 | 20 | 20.0 | 51.9 | 91 | 49.6 | 2.48 |
| 21 | 30 | 19.8 | 65.8 | 91 | 62.8 | 3.14 |

Conditions: 80° C. 2 mL volume. Concentration of complex, 25 g/100 mL. Mole ratios: ACL/Ni = 3.05; D-Lysine/ACL = 0.02; LiOEt/ACL = 0.02.

$^{(a)}$Seeds plus precipitate
$^{(b)}$mg of L-$(ACL_3NiCl_2 \cdot EtOH$ used as seed crystals
$^{(c)}$Percent of L-$(ACL)_3NiCl_2 \cdot EtOH$ minus percent of D- in product crystals
$^{(d)}$mg of L-$(ACL)_3NiCl_2 \cdot EtOH$ in product crystals
$^{(e)}$mg of L- in product crystals/mg seed crystals It will be noted by comparing Table 5 above vs. Table 4, that when D-lysine was the additive instead of L-lysine in otherwise the same operations as in Table 4, the effect of the D-lysine was to lower the rate of formation of the L-$(ACL)_3NiCl_2 \cdot EtOH$ complex, seeded by crystals of this L-complex.

TABLE 6 kinetics of Resolution of $(ACL)_3NiCl_2 \cdot EtOH$ in the Absence of Lysine

| Example No. | Time Min. | Seeds (L-) mg$^{(b)}$ | Total Product mg$^{(a)}$ | % Excess L-$^{(c)}$ | mg L-$^{(d)}$ | L-Growth Factor$^{(e)}$ |
|---|---|---|---|---|---|---|
| 22 | 10 | 20.0 | 59.2 | 91 | 56.5 | 2.83 |
| 23 | 20 | 19.7 | 83.4 | 91 | 79.6 | 3.98 |
| 24 | 30 | 19.8 | 115.6 | 61 | 93.1 | 4.65 |
| 25 | 40 | 20.3 | 192.8 | 27 | 122.4 | 6.12 |

Conditions: 80° C., 2 mL volume. Concentration of complex, 25 g/100 mL. ACL/Ni = 3.05 mole ratio $^{(a)}$Seeds plus precipitate
$^{(b)}$mg of L-$(ACL)_3NiCl_2 \cdot EtOH$ used as seed crystals
$^{(c)}$Percent of L-$(ACL)_3NiCl_2 \cdot EtOH$ minus percent of D- in product crystals
$^{(d)}$mg of L-$(ACL)_3NiCl_2 \cdot EtOH$ in product crystals
$^{(e)}$mg of L- in product crystals/mg seed crystals Comparison of this Table 6 vs. Table 4 above shows that use of L-lysine as additive (Table 4) lowers the rate of formation of the L-$(ACL)_3NiCl_2 \cdot EtOH$ complex, seeded by crystals of this L-complex, as compared to no additive (but such lowering is not as pronounced as when D-lysine is the additive per Table 5 above).

We claim:

1. In a process for resolution of a mixture of D- and L-forms of the tris (alpha-aminocaprolactam)/$NiCl_2 \cdot$ ROH enantiomeric complex—wherein R is methyl, ethyl, or isopropyl—to increase the ratio of one form of said complex in the crystalline product obtained, as compared to the ratio in the starting material, which process comprises forming a supersaturated solution of said complex; the improvement which comprises including one optically active form of lysine in said solution, namely L-lysine as crystallization inhibitor of the D-form of said complex when the L-form is desired and D-lysine when the D-form of the complex is desired; and crystallizing a portion of the complex from said supersaturated solution.

2. Process of claim 1 wherein L-lysine is included in said supersaturated solution in the range between 1 mole percent and 20 mole percent based on the content of the complex in said solution.

3. Process of claim 2 wherein the mixture of D- and L- enantiomers in the starting solution is the racemic mixture, and said solution is seeded with crystals of the racemic form of the complex.

4. Process of claim 1 wherein a strong base is provided in the reaction mixture in excess over the amount equivalent to the carboxyl groups in the lysine provided in the reaction mixture; and alpha-aminocaprolactam is provided in excess over the stoichiometrically required amount to form said complex, whereby racemization proceeds in the reaction solution simultaneously with the resolution process.

* * * * *